United States Patent [19]

Koffsky et al.

[11] Patent Number: 4,809,915

[45] Date of Patent: Mar. 7, 1989

[54] WASTE DISPOSAL APPARATUS

[75] Inventors: Robert M. Koffsky, Hopewell Junction, N.J.; Finn S. Pedersen, Telgte/Munster, Fed. Rep. of Germany

[73] Assignee: Affald International Inc., Hopewell Junction, N.Y.

[21] Appl. No.: 165,145

[22] Filed: Mar. 7, 1988

[51] Int. Cl.⁴ .............................................. B02C 18/22
[52] U.S. Cl. ........................................ 241/36; 241/99; 241/100; 241/224; 241/294
[58] Field of Search .................. 241/101.7, 36, 34, 99, 241/73, 100, DIG. 14, 186.2, 186 R, 224, 293, 294

[56] References Cited

U.S. PATENT DOCUMENTS

| | | |
|---|---|---|
| 1,706,643 | 3/1929 | Wiley . |
| 3,432,108 | 3/1969 | Enright ............................ 241/100 |
| 3,589,276 | 6/1971 | Swallert . |
| 3,750,966 | 8/1973 | Anderson . |
| 3,774,852 | 11/1973 | Edlund . |
| 3,814,332 | 6/1974 | Nakao . |
| 3,926,379 | 12/1975 | Dryden et al. . |
| 3,929,295 | 12/1975 | Montalbano . |
| 3,958,765 | 5/1976 | Musselman . |
| 3,987,972 | 10/1976 | Gladwin . |
| 4,050,899 | 9/1977 | Grabe et al. . |
| 4,269,364 | 5/1981 | Moriconi et al. . |
| 4,396,158 | 8/1983 | Olsen . |
| 4,452,358 | 6/1984 | Simpson . |
| 4,618,103 | 10/1986 | Wilson et al. ...................... 241/99 X |
| 4,619,409 | 10/1986 | Harper et al. ..................... 241/99 X |
| 4,759,508 | 7/1988 | Griffith et al. .................. 241/100 X |

*Primary Examiner*—Mark Rosenbaum
*Attorney, Agent, or Firm*—David N. Koffsky

[57] ABSTRACT

A rotary grinder is described including a hopper for receiving waste through a door, which door when closed, provides a fluid tight seal. A movable waste receptacle is provided beneath the grinder and is locked in place and weighed during the operation of the grinder. An iris diaphragm valve mates with the outlet from the grinder and, when in its open orientation, drops a sleeve into the waste receptacle thereby creating a sealed enclosure for the decontaminated waste material. Cutting blades employed by the grinder are identical and are provided with bearing shoulders which determine the amount of blade exposed when the blades are mounted on rotating arms of the grinder.

12 Claims, 6 Drawing Sheets

WASTE DISPOSAL APPARATUS

FIELD OF THE INVENTION

This invention relates generally to waste disposal apparatus and more particularly to apparatus for comminuting and decontaminating medical waste.

DESCRIPTION OF THE PRIOR ART

The problems attendant to the destruction and decontamination of hospital waste are well-known. Syringes, plastic blood bags, metal clips, hoses, etc. etc. present formidable problems in their disposal. Not only are they difficult to deal with, but also they are infected with viral and bacterial pathogens which make their handling hazardous. These items must be decontaminated, rendered harmless and disposed of to prevent the transmission of disease, to avoid accessibility of used needles and syringes and for purposes of general sanitation.

Apparatus adapted to the disposal of hospital waste is already in existence. It, however, suffers from a number of shortcomings. Some designers have, for sanitation purposes, decided upon a design wherein the entire disposal apparatus, including the waste storage apparatus, is contained within a single enclosure—thereby requiring the using hospital to dedicate a very large area for its operation. Smaller waste disposal apparatus available today exhibits substantial safety problems, including leaks and other shortcomings which make them not particularly suitable to institutional applications where relatively unskilled workers are employed as operators. Moreover, since these apparatus are employed for the disposal of glass, plastic and other implements, the wear and tear on the machines is considerable. The users are generally incapable of keeping the machines in proper adjustment. They thus require either the presence of a skilled mechanic on staff or frequent calls by the manufacturer's skilled mechanic.

In addition to being difficult to maintain, present hospital waste disposal units often use much more decontaminant then is required For instance, some units immerse the comminuted waste product in a decontaminant bath and then dispose of both the fluid and the waste together Others employ plastic waste bags which are themselves substantially filled with a decontaminating fluid and the waste material is emplaced therein. This overuse of decontaminant is unnecessary to achieve the desired decontamination creates an expensive overhead item in the continued use of the disposal units; and presents disposal problems due to the propensity of the decontaminant to pollute ground waters when the waste material is taken to a landfill.

A number of prior art patents exist disclosing various equipments for the destruction and disposal of medical waste. U.S. Pat. No. 1,706,643, granted on Mar. 26, 1926 to S. W. Wiley, is one of the earlier of these patents. It discloses a laboratory mill having a rotary cutter disposed in a cylindrical housing. The blades of the cutter are adjustable and interact with a plurality of fixed blades which are mounted in and extend from a cylindrical housing. A screen is employed to prevent material of too large a size from being dropped into a waste hopper.

U.S. Pat. No. 3,926,379, granted on Dec. 16, 1975 to Dryden et al., discloses a waste disposal device including a rotary comminuter/screen configuration somewhat similar to the Wiley structure. Here, however, disinfectant is employed in a continuous flow from a reservoir through the material being comminuted and then back to the reservoir.

U.S. Pat. No. 4,269,364, granted May 26, 1981 to Moriconi et al., describes a needle chopper wherein the chopping apparatus involves a set of rotating knives which pass beneath an aperture through which the needles are dropped. Here, the items being disposed of are disinfected while they're being chopped into particulate matter, and the disinfecting fluid is disposed of along with the waste material.

In the noted prior art, there are no teachings of how to deal with rotor "obstructions"; how to assure that the optimal amount of decontaminant is used to achieve the required decontamination operation; how to assure that the cutting knives may be installed without need for a skilled mechanic to adjust their clearances; how to assure that once the machine is energized, that it, including any waste receptacle creates a sealed environment so that pathogens and/or decontaminant cannot affect the operators.

OBJECTS OF THE INVENTION

It is an object of this invention to provide an improved waste disposal apparatus which, when energized, provides a completely sealed internal environment.

It is a further object of this invention to provide a waste disposal apparatus particularly suited for use by unskilled labor.

It is still another object of this invention to provide improved waste disposal apparatus particularly suited for hospital waste material and wherein minimal amounts of decontaminant are employed.

It is a still further object of this invention to provide a waste disposal apparatus wherein machine obstructions may be cleared automatically without operator intervention.

SUMMARY OF THE INVENTION

The above and other objects of the invention are achieved by providing a rotary grinder means within a housing having both an inlet and outlet. A hopper is mated with the inlet and is provided with an opening for receiving waste through a door, which door when closed provides a fluid tight seal and is locked during the operation of the rotary grinder. A movable waste receptacle is provided beneath the grinder means and is locked in place and weighed during the operation of the grinder means. An iris diaphragm valve is mated with the outlet from the grinder means and, when in its open orientation, drops a sleeve into the waste receptacle thereby creating a sealed enclosure for the decontaminated waste material.

The rotary grinder means is provided with a plurality of nozzles which rotate with the grinder and provide a mist which engulfs the waste being comminuted. The amount of decontaminant is thus greatly limited while at the same time, completely contacting and decontaminating the waste.

Cutting blades employed by the grinder means are all identical and are provided with bearing shoulders which determine the amount of blade exposed when the blades are mounted on rotating arms of the grinder means. When the blades are removed for sharpening, their shoulders are likewise machined to thereby maintain the distance between the shoulder and the knife edge of the blade constant. This structure enables an unskilled worker to install the blades and to avoid the need for any subsequent adjustment. Rotating blades may be further oriented at an angle to fixed blades so as to create a scissor-like action during the comminuting process.

Obstructions occur when non-comminutable objects are put in the grinder or when the waste tends to agglomerate at the grinder's input, both situations causing the grinder's speed of rotation to slow or stop. Such speed alterations are sensed and corrected by an automatic reversal of the grinding motor so that most obstructions are automatically cleared without need for operator intervention. Finally, numerous safety features are included which prevent an operator's intervention in the operation of the comminuting apparatus until it is safely in a de-energized state.

DETAILED DESCRIPTION OF THE INVENTION

Figure 1:
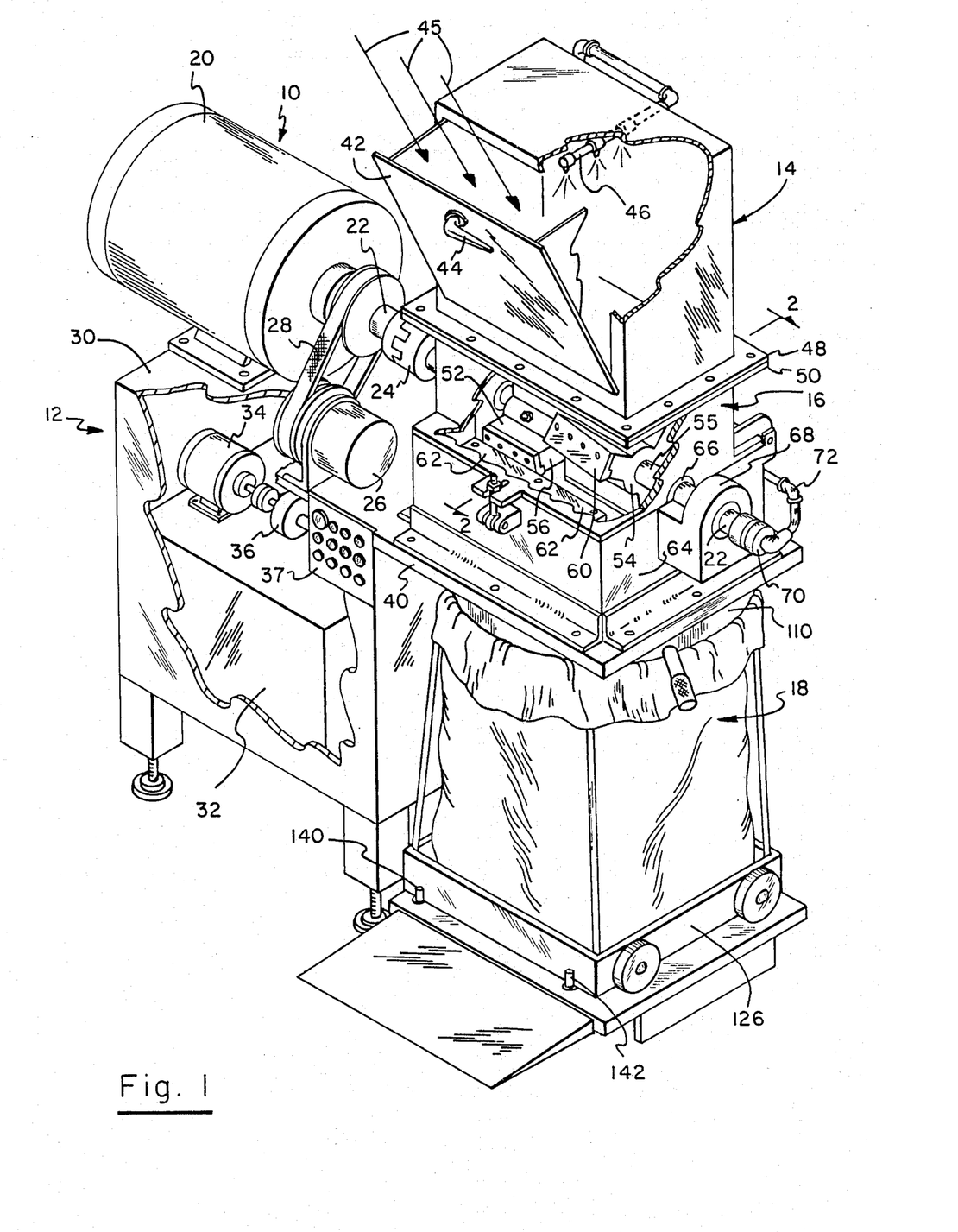
FIG. 1 is a perspective view of a comminuting apparatus in accordance with the present invention.

The invention comprises five main sub-assemblies: motor drive unit 10, decontaminant reservoir and pump assembly 12, waste/hopper assembly 14, grinder assembly 16, and processed waste receptacle and scale 18. Motor assembly 10 comprises a large AC motor 20 which is coupled via shaft 22 and union 24 to grinder assembly 16. A small DC generator 26 is coupled to shaft 22 via belt drive 28. Generator 26 is employed to provide signals which indicate both the direction and speed of rotation of shaft 22. Motor 20 is fixedly mounted on enclosure 30 which in turn encompasses and supports decontaminant reservoir 32; decontaminant pump motor 34 and decontaminant pump 36. The uppermost portion of enclosure 30 has a cantilevered portion 40 which supports both hopper assembly 14 and grinder assembly 16. An Indicator Board 37 is mounted on the side of motor assembly 12 and provides various operator and maintenance control indications.

Hopper assembly 14 includes a rotatably mounted door 42 which may be locked or unlocked by handle 44. When hopper door 42 is in its open-most position, it is adapted to receive waste material from above as indicated by arrows 45. Within hopper assembly 14 is a decontaminant nozzle assembly 46 which is employed for wash-down purposes subsequent to the operation of grinder assembly 16. Hopper assembly 14 is attached via flanges 48 and 50 to the input opening of grinder assembly 16.

Figure 2:
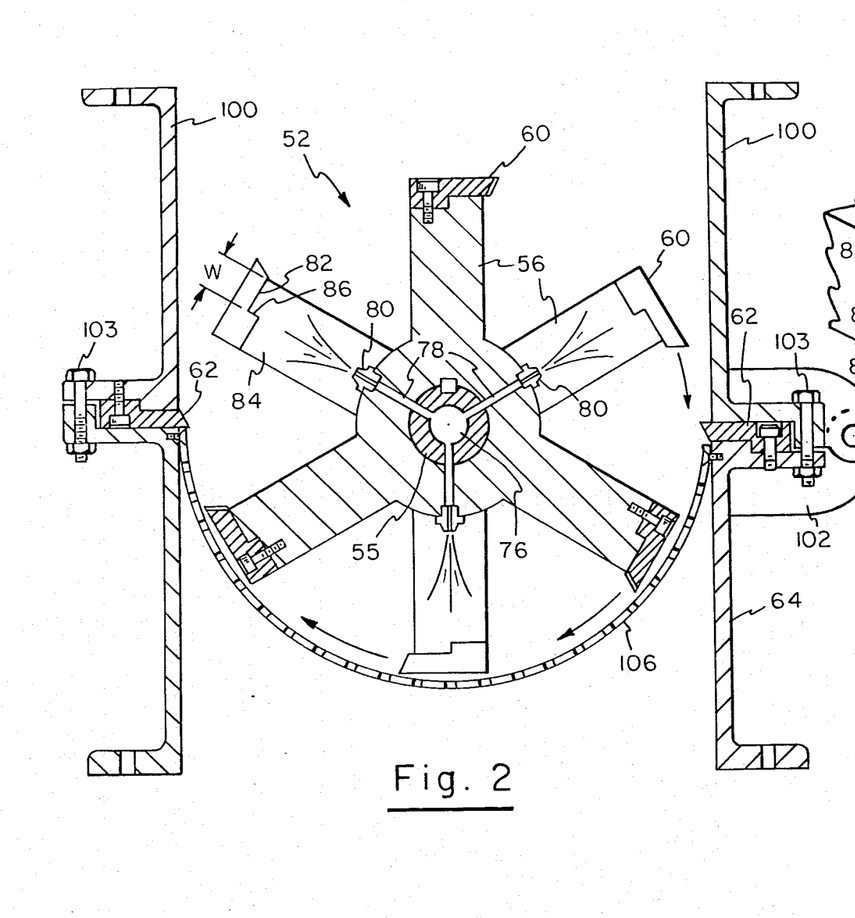
FIG. 2 is a section view taken along lines 2—2 in FIG. 1 and showing the internal rotary grinder.

A pair of rotary grinder heads 52 and 54 are mounted on shaft 55 (which is an extension of shaft 22) and are adapted to rotate in conjunction therewith. It should be realized by those skilled in the art that while only a pair of grinder heads are shown, the number may be varied in accordance with the application. Each of grinder heads 52 and 54 includes a plurality of radially extending arms 56, on the end of each of which is mounted a cutting knife 60. Also mounted within rotary grinder assembly 16 are a plurality of fixed bed knives 62 which are identical in construction to rotary cutting knives 16 but, are fixedly mounted to enclosure 64 which encloses rotary grinder assembly 16.

The right most portion of shaft 55 passes through bearing/seal assembly 66 and bearing block 68 to a rotating union 70 through which decontaminant is fed via pipe 72.

Figures 3, 3A:
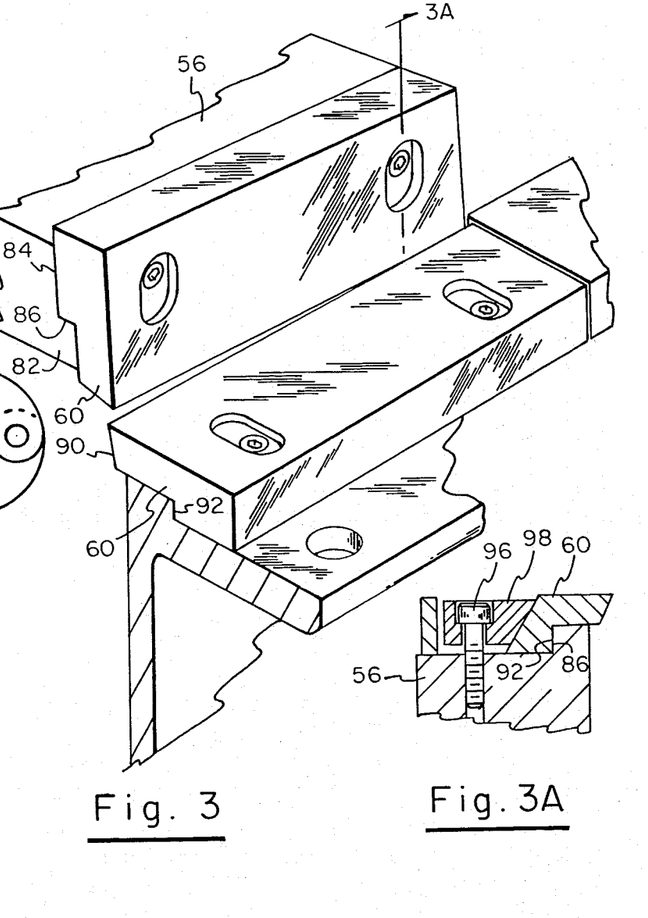
FIG. 3 is an expanded perspective detail showing the mounting of the cutting knives in the rotary grinder.
FIG. 3a is a section view of a wedge-bolt arrangement which holds down the cutting knives in FIG. 3.

Referring now to FIGS. 2, 3 and 3a, further details of rotating grinder assembly 16 will be described.

Shaft 55 is provided with an internal lumen 76 which connects, via rotating union 70, pipe 72, to decontaminant pump 36 and reservoir 32 (FIG. 1). Radial passages 78 are fed from internal lumen 76 and connect to spray heads 80. Spray heads 80 provide a fine mist spray when decontaminant is pumped via lumen 76 and passages 78. The decontaminant spray is thus widely dispersed within rotating grinder assembly 16, both by the action of the rotating motion which causes spray heads to traverse a 360° arc and by the motion of arms 56 and blades 60 as they impact upon and further disperse the spray.

Referring now to FIGS. 2 and 3 in conjunction, the distal ends of each of radial arms 56 is provided with an extended portion 82, an indented portion 84 and a bearing shoulder 86. The width W of extended portion 82 is fixed and is the same for all arms 56. It is that distance (i.e. the distance W between shoulder 86 and the outermost extremity of extended portion 82) which determines the amount of exposure of the cutting surfaces of knives 60. As aforestated, each of knives 60 is identical. When any of knives 60 must be removed for sharpening or refurbishment, not only is its cutting edge 90 machined, but so also is its shoulder 92 machined so that the distance between shoulder 92 and cutting edge 90 (see FIG. 3) remains constant in its relation to the distance W. Thus, when any knife 60 is re-emplaced into position, the amount of cutting edge 90 which is exposed requires no adjustment and is automatically correct.

In order to make the cutting action of the rotary grinder assembly more efficient, the knives 60 mounted on arms 56 are slightly canted by virtue of the fact that raised portions 82 are also canted. Thus, when the cutting edge of a rotating knife comes into close proximity to a bed knife (as shown in FIG. 3) a scissor like action occurs thereby increasing the effectiveness of the comminuting action of the rotary grinder.

Referring briefly to FIG. 3a, it will be seen that each of knives 60 is held in place by a cap screw 96 which in turn forces wedge bolt 98 against the opening in blade 60. Each wedge bolt 98 acts to force the shoulder 92 of each of blade 60 against bearing surface 86 on arm 56.

Referring again to FIG. 2, it will be noted that the upper portion 100 of the rotary grinder assembly 16 enclosure is pivotally mounted by hinge assembly 102 to the lower portion 64 of the enclosure. Thus, when the bolts 103 are removed which hold together the upper portion 100 and lower portion 64 of the grinder assembly enclosure, it may be opened to enable access to the blades and cutter assembly.

Affixed in the outlet of rotary grinder assembly 16 is a screen 106 which prevents particles larger than the size of the apertures in screen 106 from escaping.

Figure 4:
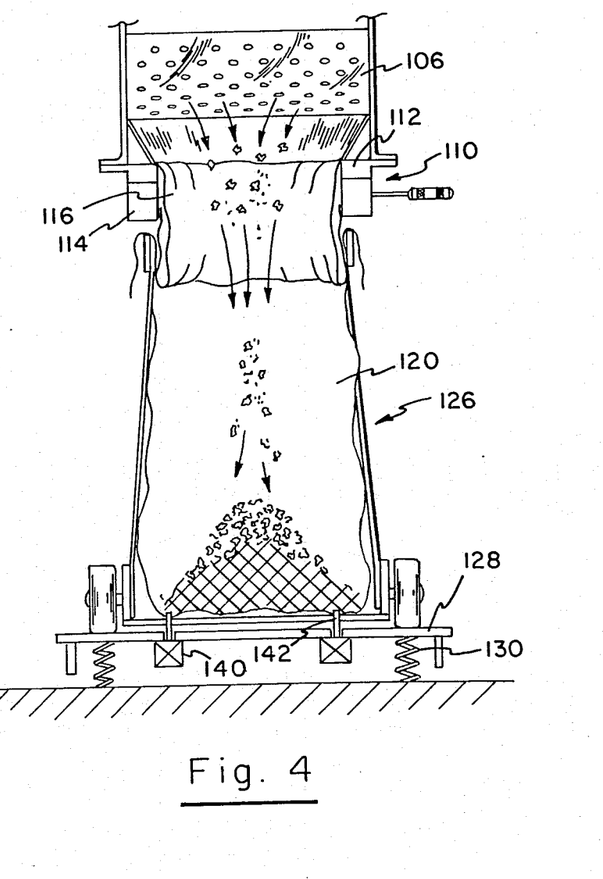
FIG. 4 is a frontal schematic and partial section view of the waste receptacle and the iris valve when the valve is in its open position.
Figure 5:
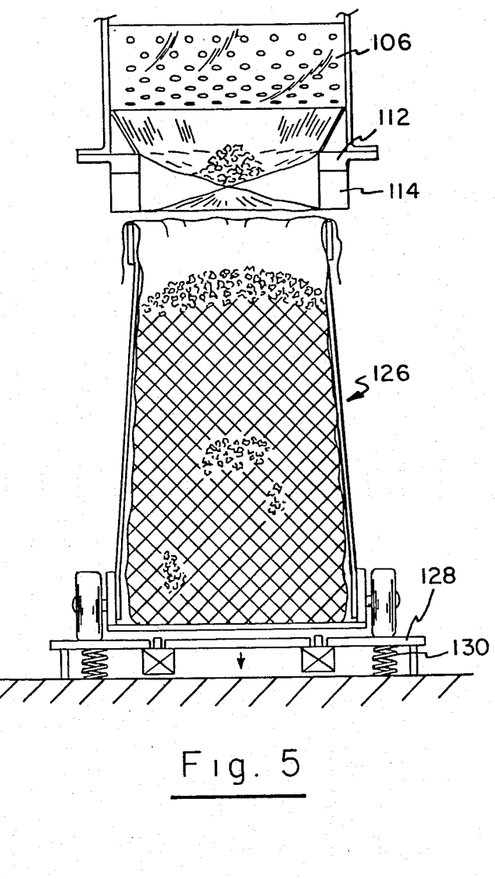
FIG. 5 is a frontal schematic and partial section view of the waste receptacle when it is filled and the iris valve is closed.

Attached to the outlet orifice of rotary grinder assembly 16 is an iris diaphragm valve 110 which is shown in schematic detail in FIGS. 4 and 5. Iris diaphragm valves are known in the art and can be obtained in various diameters and configurations (e.g. "Mucon" iris diaphragm valves are available from KEMUTEC Inc., 130 Wharton Road, Keystone Park, Bristol, Pa. 19007). In brief, diaphragm valve 110 includes three major components, an upper fixed ring 112, a lower rotatable ring 114, and a sleeve 116 which is attached to both upper and lower rings 112 and 114. When lower ring 114 is rotated to open the valve, sleeve 116 protrudes down as shown in FIG. 4. When the valve is closed, i.e. the lower ring is rotated to draw sleeve 116 taut, as shown in FIG. 5, the sleeve prevents any material from passing therethrough. The diaphragm is preferably of a nylon material which has been coated with a moisture impervious polymer or rubber material. The diaphragm may also comprise two concentric sleeves, one of a high strength material and the other of a water proof material, e.g. rubber.

As shown in FIG. 4, a waste receptacle bag 120 rests on cart 126 much in the same manner as a garbage bag rests within a garbage pail. Cart 126 is supported by a shelf 128 which in turn sits on a scale 130 schematically shown.

As the particulate matter loads cart 126, scale 130 is depressed until it indicates that the receptacle has reached a predetermined weight at which point, signals are given which stop the grinder and indicate to the operator to close iris valve 110. It should be noted, that when iris valve 110 is in its open position, sleeve 116 droops into receptacle bag 120 and causes a seal to occur between the uppermost portion of bag 120 and sleeve 116. Thus, during operation, a completely sealed environment is provided for both the decontaminant and the material being comminuted. This is accomplished without need for vacuum or other atmospheric control and is effective for worker protection.

Figure 6:
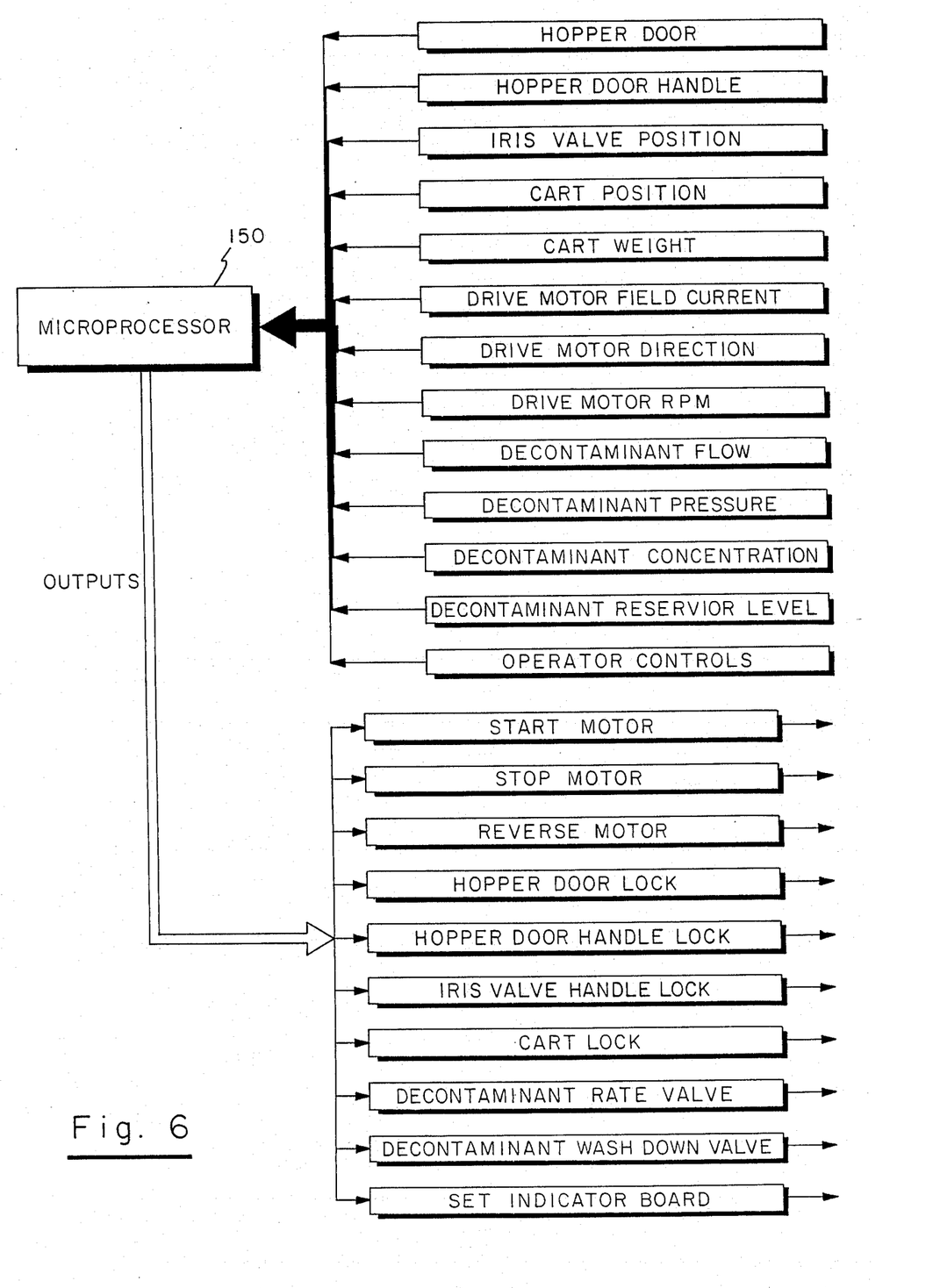
FIG. 6 is a partial schematic showing the various inputs to a microprocessor which controls the operation of the invention.

Referring now to FIG. 6, the controls for the invention will be described. It should be noted, that none of the electrical solenoids, locks, start button, sensors, micro switches etc. are shown in the drawings to prevent undue complication thereof. Micro processor 150 may be any type of process control processor which is adapted to monitor a multiplicity of signal inputs and is able to provide a number of output commands to control circuitry for the operation of the system. In this instance, a preferred microprocessor is the SLC 150 manufactured by the Alan/Bradley Company. The SLC 150 is capable of receiving 20 inputs and providing 12 outputs. As shown in FIG. 6, a plurality of inputs are applied to microprocessor 150 from various points in the invention. Microswitches (not shown) provide indications of the positions of the hopper door, hopper door handle, iris valve 110 and cart 126. Scale 130 provides an indication of the weight of cart 126 whereas a current indicator connected to the windings of motor 20 provides an indication of the motor's field current. Indications of drive motor direction and revolutions per minute are provided from generator 26. Indications of decontaminant flow, pressure, concentration and reservoir level are provided from transducers contained within the decontaminant reservoir system 2 (not shown).

Microprocessor 150 in response to the various aforementioned inputs, provides a plurality of control output signals. Those also are indicated in FIG. 6 and include start and stop motor signals, a reverse motor direction signal, a signal to lock the hopper door and in addition, to lock the hopper door handle; a signal to lock the iris valve handle and to lock the cart into place. In addition, there are outputs which control the decontaminant rate of flow and the operation of decontaminant wash down nozzle 46.

Figure 7:
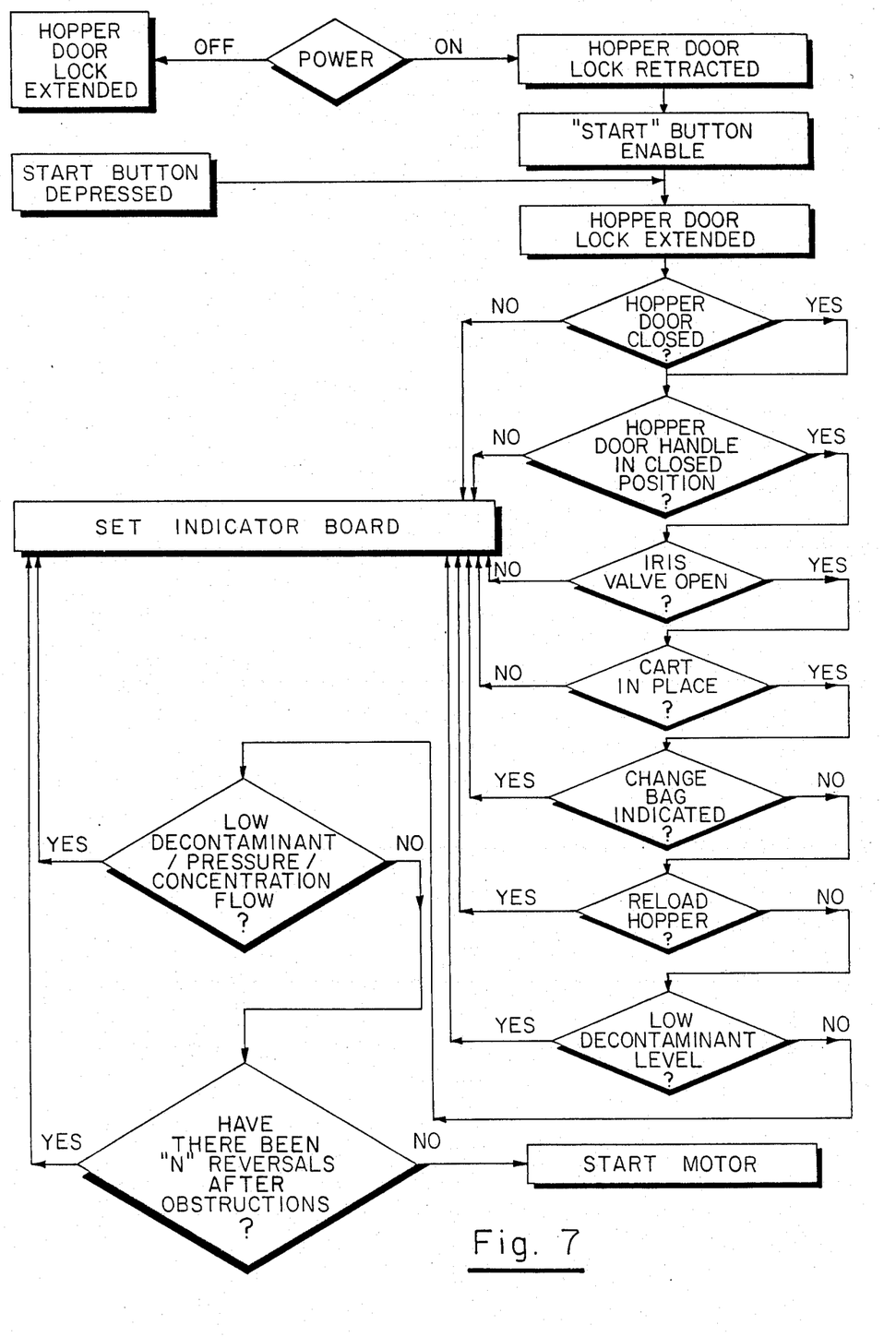
FIG. 7 is a flow diagram describing the start sequence of the invention.

Referring now to FIG. 7, the operation of microprocessor 150 in a "start" sequence will be described. As will be seen from a review of flow chart of FIG. 7, if the power to the system is off, the hopper door lock is extended and the hopper assembly 14 is not accessible to the operator. If the power is on, the hopper door lock is retracted and the start button is enabled. At this point, the hopper is available for loading, which action may be taken by the operator.

Once the hopper has been filled by the operator, the hopper door is closed and the start button depressed. This causes the hopper door lock to be extended and a sequence of interrogations to occur on the part of microprocessor 150. It first questions whether the hopper door has been closed and if it has, goes on to determine that the hopper door handle is in its closed and locked position. Assuming that it is, microcomputer 150 continues to determine whether the iris valve is open and whether the receptacle cart is in place. Microcomputer 150 then determines whether the scale indicates that the waste receptacle is full in which case it halts the start procedure and sets an indicator on indicator board 37 that the bag must be changed before the start procedure can continue.

If microcomputer 150 finds that the "change waste bag" signal is not indicated, it proceeds to determine whether the "reload hopper" signal is yes or no. The "reload hopper" signal will have been set to the yes state by an output from generator 26 indicating that motor 10 was up to full speed and that its field current was within the limits which occur with an unloaded grinder. In such case the start sequence halts and a "reload hopper" indication appears on indicator board 37. The "reload hopper" signal is set to the "no" state when hopper door 42 is opened after a "reload hopper" indication has been given.

Microcomputer 150 continues to inquire whether the decontaminant level is at its proper state; whether there is adequate decontaminant flow, pressure, and concentration and whether there have been a number of obstruction clear operations (to be hereinafter described in greater detail). If in each case, the level of decontaminant is found to be proper, there is decontaminant flow and proper pressure and concentration levels are sensed and there have not been any reversals after an obstruction signal, then motor 20 is started and the grinding operation commences.

As aforestated, while not shown, each of the access doors to the system is monitored by a mounted microswitch which indicates whether the door is open or closed and whether the respective locks involved in securing the door are engaged or not engaged. Microswitches are mounted on iris valve 110 to enable microcomputer to sense when the iris valve is in its open or closed state. When cart 126 is in place, one of its wheels depresses a microswitch thereby indicating the "cart in place" signal to microcomputer 150. The "change bag" indication is received from scale 130 when its weight indication exceeds a predetermined limit. The decontaminant level and decontaminant flow, pressure and concentration indications are received respectively from a level indicator in decontaminant tank 32 and a flow valve and concentration cell in one of the decontaminant pipes leading from 36.

Figure 8:
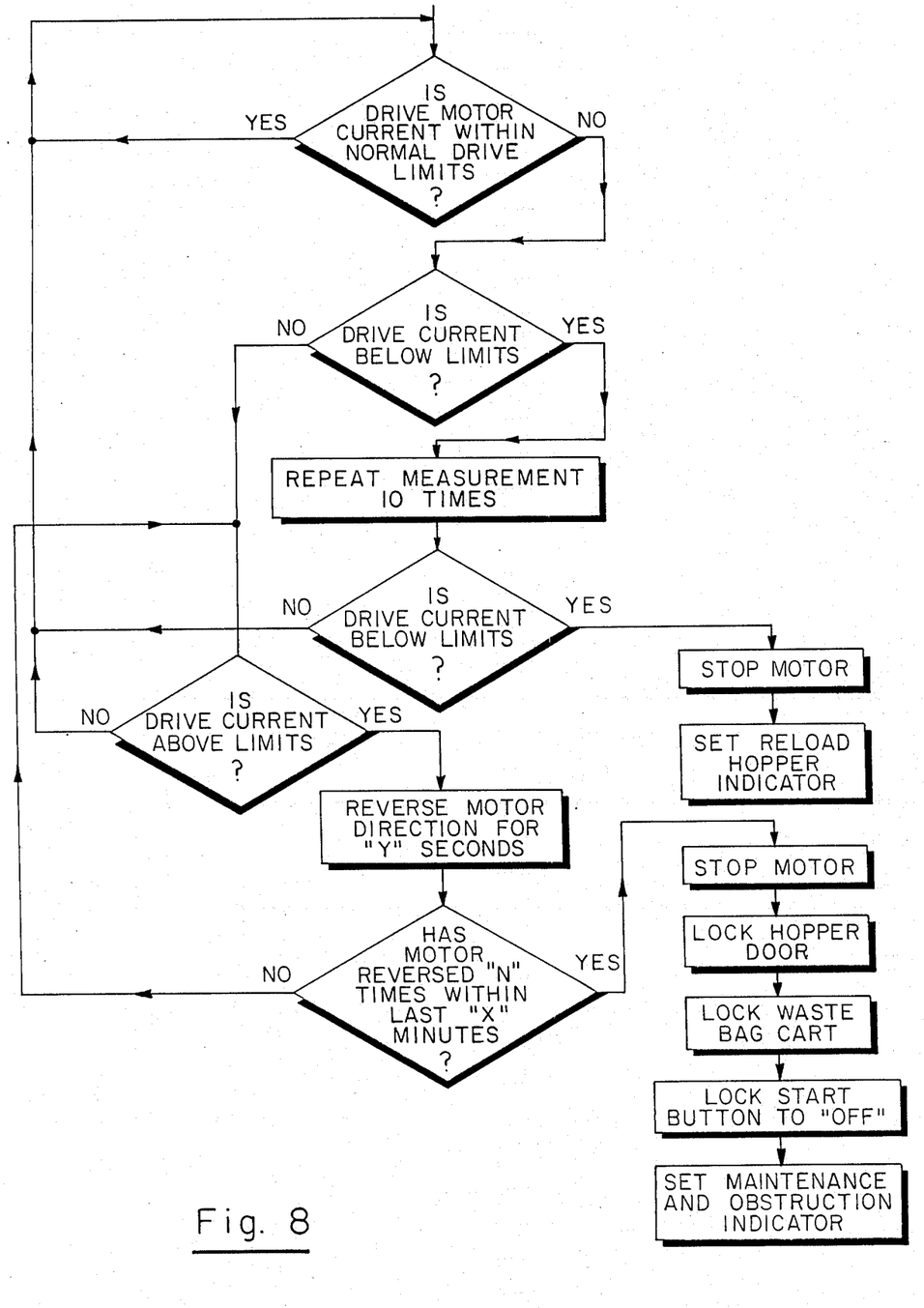
FIG. 8 is a flow diagram illustrating an obstruction-clear sequence which is initiated when an obstruction is sensed.

Turning now to FIG. 8, the system's method of clearing an obstruction will be described. Microcomputer 150 continually determines whether the field current of drive motor 20 is within its normal limits. So long as it is, the test is repeated on a continuing basis. If there is an out-of-limits indication, the computer 150 determines whether the field current is below its limits which indicates that drive motor 20 is in a "no load" situation. If that is the case, the measurement is repeated a number of times (e.g. 10) to determine whether the drive current still remains below its operating limits. Assuming a "below limits" is indicated, motor 20 is stopped and the "reload hopper" indicator is set thereby informing the operator that additional material can be added to the hopper. Conversely, if at any time the drive current is indicated as not being below limits, it is then tested to determine whether it is above limits. If it is found to be above limits, that is an indication that an obstruction has occurred and that the field current of drive motor 20 has risen to an unacceptable level. In such case, an instruction is issued by microcomputer 150 to reverse motor 20's direction for a short period of time (e.g. 10 seconds). After a reversal, Microcomputer 150 determines whether the motor has had N "reverse cycles" within the last x minutes (e.g. where N equals 3 and x equals 2). If that is not the case, motor 20 is caused to rotate in its normal direction and its field current is again tested to determine whether it is above limits. If that is the case, the reversal subroutine is then commenced in another attempt to clear the obstruction. After N times, the program automatically assumes that maintenance assistance is required to clear the obstruction. In that case, the motor 20 is stopped, hopper door 42 is locked, cart 126 is locked and the start button is locked in the off position. Finally, "maintenance require" and "obstruction" indications are set on indicator board 15 and a maintenance person must be called to clear and reset the machine.

We claim:

1. Comminuting apparatus particularly suited to the disposal of medical waste comprising:
   rotary grinder means enclosed within a housing having inlet and outlet openings, for comminuting waste into particulate matter, said rotary grinder means provided with a plurality of removable cutting knives;
   hopper means mated with said inlet opening for receiving waste through a door, which door, when closed providing a fluid-tight seal;
   a movable waste receptacle juxtaposed to said outlet opening to receive comminuted waste from said rotary grinder means, said waste receptacle provided with a sealable opening; and
   an iris diaphragm valve mated with said outlet opening, said valve including two rings rotatably movable with respect to each other and a sleeve affixed therebetween, said valve being open when said rings are rotatably arranged to allow said sleeve to fall slack, said sleeve, when slack, extending through said waste receptacle's opening and providing a seal between the interior of said receptacle and the outside environment, whereby a fluid tight interior environment is provided for said comminuting apparatus.

2. The invention as defined in claim 1 wherein said rotary grinder means includes:
   rotating shaft means; and
   a plurality of radially extending arms affixed to said rotating shaft means, the outermost portion of each said arm including mounting means for a cutting knife; and
   decontaminant nozzle means for bathing said particulate matter with a flow of decontaminant.

3. The invention as defined in claim 2 wherein said decontaminant nozzle means are affixed to said rotating shaft means and said shaft means includes a lumen therein for providing decontaminant to said nozzle means.

4. The invention as defined in claim 3 further including means for providing decontaminant to said lumen only when said rotary grinder means is in operation.

5. The invention defined in claim 1 wherein each said cutting knife has a cutting edge and a shoulder, the distance between said cutting edge and shoulder being a predetermined constant.

6. The invention as defined in claim 5 wherein each said radially extending arm has a leading edge and a bearing surface, which surface is adapted to mate with said shoulder of a cutting knife, the distance between said leading edge and bearing surface being less than said predetermined constant to allow a portion of the cutting edge of said cutting knife to extend past said leading edge when said knife is mounted on said arm.

7. The invention as defined in claim 6, further including bed knife means fixedly mounted within said housing and oriented to expose a cutting edge to cutting knives mounted on said radially extending arms, and positioned to create a cutting action in combination with said bed knife means.

8. The invention as defined in claim 7 wherein the bearing surface on a radial arm is oriented at an acute angle with respect to the orientation of said bed knife's cutting edge, whereby a cutting knife mounted thereon has its cutting edge interact with a bed knife's cutting edge with a scissor type action.

9. The invention as defined in claim 8 wherein each said bed knife is identical with said cutting knives mounted on said radially extending arms and further including a plurality of bed knife mounting means, each of which includes a leading edge and a bearing surface upon which the shoulder of a bed knife bears when said bed knife is mounted thereon, whereby a predetermined portion of the cutting edge of said bed knife is exposed past said leading edge.

10. The invention as defined in claim 1 further comprising:
    motor means connected to said rotary grinder means;
    energizing means connected to said motor for causing said motor to operate said rotary grinder means;
    means for generating a grinder obstruction indication; and
    control means responsive to an obstruction indication to institute an obstruction clear cycle and to reverse the direction of rotation of said grinder means for a predetermined period, and then again to reverse said direction of rotation to a cutting direction, said control means responsive to additional obstruction indications to repeat said obstruction clear cycle N times and to then dis-enable said energizing means in response to an occurrence of the N+1 sequential obstruction indication.

11. The invention as defined in claim 10 wherein said N obstruction cycles must occur within a preset interval before said energizing means is dis-enabled.

12. The invention as defined in claim 10 wherein said control means additionally locks said hopper means and said movable waste receptacle when said energizing means is dis-enabled in response to the occurrence of said N obstruction cycles.

* * * * *